United States Patent [19]

Guisan Seijas et al.

[11] Patent Number: 5,268,271

[45] Date of Patent: Dec. 7, 1993

[54] METHOD FOR THE SYNTHESIS OF SEMI-SYNTHETIC ANTIBIOTICS IN THERMODYNAMICALLY CONTROLLED WATER-COSOLVENT ORGANIC MISCIBLE APOLAR SYSTEMS BY USING PENICILLIN G ACYLASE

[75] Inventors: Jose M. Guisan Seijas; Roberto Fernandez Lafuente; Gregorio Alvaro Campos; Rosa M. Blanco Martin; Cristina Molina Rosell, all of Madrid, Spain

[73] Assignee: Cosejo Superior de Invetigaciones Certificas, Madrid, Spain

[21] Appl. No.: 767,044

[22] Filed: Aug. 2, 1991

Related U.S. Application Data

[63] Continuation of PCT/01/000,046, Dec. 12, 1990.

[51] Int. Cl.⁵ .......... C12P 37/00; C12P 35/00/35/06; C12N 9/84
[52] U.S. Cl. ........................ 435/43; 435/44; 435/45; 435/46; 435/47; 435/49; 435/117; 435/118; 435/176; 435/177; 435/178; 435/179; 435/180; 435/228; 435/229; 435/230
[58] Field of Search .................. 435/228, 229, 43, 230, 435/117-118, 84, 120, 46, 84, 47, 176-180

[56] References Cited

U.S. PATENT DOCUMENTS

| | | | |
|---|---|---|---|
| 3,337,415 | 8/1967 | Brandl et al. | 435/230 |
| 3,766,009 | 10/1973 | Vitale | 435/230 |
| 3,925,157 | 12/1975 | Hamsher | 435/180 |
| 3,945,888 | 3/1976 | Takahashi et al. | 435/230 |
| 4,167,446 | 9/1979 | Huper | 435/179 |
| 4,267,273 | 5/1981 | Smith | 435/181 |
| 4,340,672 | 7/1982 | Kondo et al. | 435/45 |
| 4,693,977 | 9/1987 | Wolfe et al. | 435/43 |
| 5,079,146 | 1/1992 | Fuganti et al. | 435/230 |
| 5,104,800 | 4/1992 | Crawford | 435/47 |

FOREIGN PATENT DOCUMENTS

| | | |
|---|---|---|
| 3507403 | 9/1986 | Fed. Rep. of Germany . |
| 2188608 | 1/1974 | France . |
| 2021119 | 11/1979 | United Kingdom ............... 435/230 |
| 2146336 | 4/1985 | United Kingdom ............... 435/230 |

OTHER PUBLICATIONS

Abbott "Preparation of Pharmaceutical Compounds by Immobilized Enzymes of Cells" Adv. Appl. Microbiol. vol. 20 1976 pp. 203-257.

Mahajan "Review Penicillin Acylases" Appl. Biochem & Biotech vol. 9 1984, pp. 537-554.

Svedas et al. "Enzy. Microb. Tech" 1980 vol. 12 Apr. pp. 138-144.

Margolin et al. "Bioch. Biophys. Acta" 616 (1990) pp. 283-289.

Chem. Abst., vol. 90 No. 19 (May 7, 1979) CA90: 150291t Yoshio et al.

Chem. Abst., vol. 93 (Dec. 22, 1980) No. 25 CA#93: 236827w Kato et al. Agricul. Biol Chem 44 (4) 821-5 (1980).

*Primary Examiner*—Herbert J. Lilling
*Attorney, Agent, or Firm*—Darby & Darby

[57] ABSTRACT

Synthesis of semi-synthetic monobactamic or β-Lactamic antibiotics by using derivatives stabilized by various methods of penicillin G acylase from various microbial sources according to a thermodynamically controlled strategy in monophase water/cosolvent organic apolar systems, wherein the concentration of the cosolvent varies between 30% and 90%, the temperature between −10° C. and 50° C., the pH between 4.5 and 8.5, with concentrations of the antibiotic nucleus between 0.5 an 875 mM and acyl donor between 0.2 mM and 1M, with a relationship antibiotic ring/activated or free acyl donor, using a buffer between 0 and 1M. Application to the pharmaceutical industry.

15 Claims, No Drawings

METHOD FOR THE SYNTHESIS OF SEMI-SYNTHETIC ANTIBIOTICS IN THERMODYNAMICALLY CONTROLLED WATER-COSOLVENT ORGANIC MISCIBLE APOLAR SYSTEMS BY USING PENICILLIN G ACYLASE

This application is a continuation of PCT 01/000,046 filed Dec. 12, 1990.

SPECIFICATION

A large number of condensation products with the final destination in food, fine chemistry or the pharmaceutical industry are normally synthesized by chemical methods, where the use of very polluting cosolvents is normally required. The need to protect the environment has caused a big increase in the search for alternative less polluting routes. In this framework, enzymatic engineering is revealed as a possible alternative.

In the case of semi-synthetic antibiotics, the use of penicillin G acylases for the synthesis thereof also has a series of advantages. Among those we can point out that there is no need to protect the carboxyl group of the antibiotic nucleus, nor the group in α of the acyl donor (such as for example in the case of phenylglycine, homopthalic acid, etc.) or the groups in any of the other positions (substituents of the ring of many thiazoles, imidazoles, etc,) that the reaction is stereospecific (important when the acyl donor is chiral such as phenylglycine or mandelic acid and), that the reaction conditions are mild.)

Penicillin G acylase is the enzyme normally used by pharmaceutical industries as the catalyst of the hydrolysis reaction of penicillin G to obtain 6 aminopenicilamic acid (6APA), starting point for the synthesis of many β-lactamic antibiotics. For many years now, penicillin G anylase has been attempted to be used as a catalyst of the second part of the process, the synthesis of semi-synthetic antibiotics (M. Cole in Biochem. J. (1969)115, 757), up to now without much success. Given that the production, purification methods etc. of this enzyme from very diverse microbial sources are already known and used normally by pharmaceutical firms, the implantation of the same in other different reactions, in this case the synthesis of semi-synthetic antibiotics, seems simple.

Penicillin G acylase can catalyze the synthesis of semi-synthetic antibiotics according to various strategies (Kasche in Enzyme Microb. Technol, 1986, vol 8, (4.16.)) Hereinafter we will comment on the main ones.

In kinetically controlled synthesis, an activated acyl donor (in the form of an amide or, more often, an ester) is used to obtain a maximum transitory yield of product removed from balance concentrations. This is one of the more popular strategies (V. Kasche in Biotechnology Letters, 1985, Vol. 7 No. 12; T. Takahashi, K. Kato, Y. Yamazaki and M. Isono in The Japanese Journal of Antibiotics Dec. 1977, . . .), basically due to the mild reaction conditions used, which permit the use of unstabilized enzymes and enzymatic derivatives, and to the high activity that the enzyme shows in these conditions. A fact to be pointed out is that the maximum transitory yields obtained depend on the enzyme used. This synthesis strategy has not achieved up to the moment sufficiently good results (T. A. Savidge in Drugs and the Pharmaceuitcal Sciences, Vo. 22, 1984.) One way to improve them seems to be the use of organic cosolvents in the reaction medium, which implies some more drastic reaction conditions in which the stability of the enzyme begins to be important. Few studies have gone in this direction. (Kasche in Methods in Enzymology, 1987, Vol. 136, (26) and in Biotechnology Letters Vol. 7 No. 12 (877–882.))

The other synthesis strategy that we will consider is the thermodynamically controlled one. In it the yield obtained is given by the thermodynamic constant. We can carry out the reaction without the need of activating the acyl donor. If we use an activated subtrate, we can remarkably improve the rate of the process. This type of strategy has two main types, depending on whether the system is mono-phase or bi-phase. In this case, the use of one acylase derivative or another (be it a different bacterial source of the enzyme or method of preparation of the derivative will vary) only the rate of the reaction.

In the thermodynamically controlled synthesis in bi-phase systems, a water inmiscible cosolvent is used in which the antibiotic has a better solubility than in water, raising this way the yield upon removing the product from the reaction medium. In this strategy a very fine control of the water activity is required.

In thermodynamically controlled synthesis in monophase systems miscible organic cosolvent/water mixtures are used to displace the balance in the direction of the synthesis, starting from the two unmodified substrates. We consider that this type of system is the one to choose as long as it is possible to use it.

The main advantage that it has over the other two synthesis strategies is that it is much simpler, which permits a better design of the reactor and of the reaction.

Thus, with regard to the kinetically controlled synthesis, we can say that thermodynamically controlled synthesis:

1. It does not require the activation of the acyl donor, whereby at all times only the antibiotic ring, acyl donor and antibiotic are in the medium. The ester or amide of the acyl donor would have to be added to the kinetically controlled one.

2. In the event of using an activated acyl donor in the form of ester or amide, we can obtain a rate similar to that of the kinetically controlled systems and at the end the concentration of the acyl donor will be very low, if the activator is carefully chosen. In kinetically controlled synthesis, normally the maximum yield can still be attained even with a large amount of acyl donor remaining in the medium.

3. The yield obtained is stable with regard to the transitory yield that is obtained in kinetically controlled synthesis.

4. The yield that is obtained is constant without dependence on the state of the catalyst. The deactivation of this alone will modify the rate with which the balance is obtained. In kinetically controlled synthesis the yield can vary over time, depending on whether the enzyme is deactivated.

5. The overall yield of the reaction can be improved by raising the concentration of the two substrates simultaneously, or the yield can be improved by increasing the concentration of the acyl donor only (cheaper, stabler and, in many cases, more soluble.) In kinetically controlled synthesis it can only be improved by increasing the concentration of the antibiotic ring.

6. The reaction conditions can vary throughout a process for the purpose of improving the rate of the reaction without losing any yield. In kinetically controlled synthesis this would hamper even more the design of the reactor.

7. Many antibiotics seem to be very favourable cases for this type of synthesis strategy as the pk of carboxyl and of amine are very distant (as we will see later on this is very important for the yields of this type of synthesis to be acceptable.)

8. If we obtain, according to point 4, yields close to 100% for the antibiotic nucleus, the separation of the antibiotic from the reaction mixture will be very simple: it will only be necessary to separate the antibiotic from the excess acyl donor.

With regard to thermodynamically controlled synthesis in bi-phase systems, thermodynamically controlled synthesis in mono-phase systems has the following advantages:

1. Control of the pH is simpler in mono-phase systems than in bi-phase systems.

2. The concentration of water in mono-phase systems can be considered constant throughout the reaction, while it requires a very fine control in bi-phase systems.

3. Synthesis in bi-phase systems must be carried out statically with vigorous stirring. Synthesis in mono-phase systems allow the continuous or static design.

4. In the bi-phase system a large part of the volume of the reactor may not be used, since in many cases the water/cosolvent ratio must be very high and therefore the tank proportion where enzyme can be used must be very reduced.

DESIGN OF THE SYNTHESIS REACTION

Up to now, the results obtained with this synthesis strategy have been very poor (B. McDougall, P. Dunmil and M. D. Lilly in Enzyme Microb. Technol., 1982, Vol. 4, (114–115)) despite the good initial perspectives. We consider that only a joint design of the penicillin G acylase derivatives and the synthesis reaction make it possible to work in a broad enough margin of conditions to obtain good results, as we will see throughout this introduction.

The reaction that we present in this patent can be expressed in the general way as:

$$K_{ap} = \frac{(ANTIBIOTIC) \cdot (H_2)}{(NUCLEUS)_Q \cdot (DONOR)_O}$$

$$K_{ter} = \frac{(ANTIBIOTIC) \cdot (H_2O)}{(NUCLEUS \cdot NH_2) \cdot (DONOR \cdot COOH)}$$

If we make $$F = \frac{(NUCLEUS \cdot NH_2) \cdot (DONOR \cdot COOH)}{(NUCLEUS)_O \cdot (DONOR)_O}$$

$$K_{ap} = K_{ter} \cdot F$$

Therefore, we must keep in mind that only the nonionic forms intervene in the balance. Therefore, the differences between the pKs of the two substrates must be as small as possible. The ideal thing would be that the pK of the amine were lower than the pK of the carboxyl. In some given conditions, the main options that we have to improve the yield are:

Reduce the concentration of the undesired product, in this case $H_2O$.

Have F as close to 1 as possible, in such a way that the apparent constant is as similar as possible to the actual thermodynamic constant.

These two effects are obtained by adding organic cosolvents to the medium: we will reduce the water activity and we will increase the percentage of non-ionized forms, basically of the acyl donor, as a result of the increase of its $pK_{ap}$ due to the greater apolarity of the medium which stabilizes the non-ionic forms.

The second of these effects is the main one and will increase the greater the apolarity of the cosolvent and its concentration. In this way we can manage to raise the pK of the carboxyl above the pK of the amine, it being possible to find pH conditions in which practically all the amine is in the non-ionized form, but in which we have a very large amount of protonated carboxyls.

However, when the design of a reaction with an enzyme is done, it is necessary to consider the possible deleterious effects of the cosolvent on the enzyme itself.

These possible effects can be divided into two types:

1. Those that affect the three dimensional structure of the enzyme, either immediately, causing changes in the activity of the enzyme or by varying the rate of reaction in the long run, through changes in stability.

2. The possible uni- or multi-pointwise direct interactions with certain residues of the enzyme involved in the catalytic activity of the enzyme, causing the inhibition thereof. This effect is very important in the case of penicillin G acylase.

Unfortunately, the deleterious effects of the cosolvents on penicillin G acylase go in the same direction as the positive effect on the thermodynamic constant: they become more drastic as we increase the apolarity and the concentration of the same. (G. Alvaro, doctoral thesis, "Universidad Autónoma," 1988.)

Therefore, the appropriate choice of the cosolvent is a critical factor when effecting an adequate design of this synthesis reaction.

The use of stabilized derivatives will protect the enzyme from part of the first effects, but only by chance can the second ones be avoided.

Besides, in the case of antibiotic nuclei it is necessary to take well into account the solubility of these molecules, as well as their stability in the different reaction conditions.

For this reason, we consider that a design of this reaction that is useful in practice must consider at least five points:

1. Activity of the enzymatic derivative DESIGN OF THE

2. Stability of the enzymatic derivative CATALYST

3. Solubility of the antibiotic nucleus DESIGN OF THE

4. Stability of the antibiotic nucleus REACTION and of the antibiotic

5. Thermodynamics of the process

Obviously, the greater the stability and activity of our derivatives, less important will points 1 and 2 be in the engineering of the reaction and the greater the possibilities of finding suitable conditions of points 3, 4 and 5 will be for each antibiotic.

In each case, depending on the acyl donor and on the antibiotic nucleus it will be necessary to study in an integral manner the optimal conditions for the above five points: pH, T, % and nature of the cosolvent, ionic force . . . , reaching compromising situations, which normally will not have the optimums of any of the parameters in particular.

It becomes obvious that some conditions in which the operative life of the reactor is very short should be rejected, no matter how good the results obtained are (as would happen if we introduce penicillin G acylase soluble in a mixture of 70% apolar cosolvent/30% acetate, at a pH of 5° and 50° C.) The use of conditions resulting in a highly stable enzymatic derivative, but results in low solubilities of the substrates or low yields, as what happens in water or in mixtures of water/mild cosolvents should also be repeated.) With regard to activity, some conditions in which the inhibition of the cosolvents, products or substrates block the enzymatic activity, even the balance conditions cannot be attained.

If we do not use any cosolvent, the stability of the enyme is good, and so is its activity, but only some acceptable yields will be obtained in some very limited pH margins (J. O'Sullivan and C. A. Aklonnis in The Journal of Antibiotics, July 1984).

The use of mild cosolvents, such as glycerine, ethyleneglycol or polyethylenglycol hardly increases the margin of usable conditions. Even high concentrations (45% of ethyleneglycol, B. McDougall, P. Dunnill and M. D. Lilly in Enzyme Microb. Technol., 1982, Vol. 4), hardly effects the pKs of the acyl donors and the obtained results are not good enough for industrial use.

Nor is the use of very apolar cosolvents, but at low concentrations sufficient to obtain satisfactory results (20% acetone or dimethyl sulfoxide: V. Kasche in Methods in Enzymology, 1987, Vol. 136 (26.)).

Therefore, we consider that despite the serious deleterious effects of apolar cosolvents, it is essential to work with them (methanol, butanediol, ethanol, acetonitrile, acetone, tetrahydrofuran, dimethylformamide, dioxane, dimethylsulfoxide . . . ) at high concentrations, between 30 and 90%. Only these drastic conditions will have a sufficient affect on the pKs of the acyl donors (R. Fernández-Lafuente, G. Alvaro and J. M. Guisán, manuscripts in preparation.) Logically, only penicillin G acylase derivatives with a high stability and activity can be used on an industrial scale and even, in many cases, in the laboratory. In this way we can obtain some good yields in a broad scale of pH, T, etc. which make it possible to find practical values of solubility and stability of substrates and products.

The optimum pH and T conditions for solubility and stability of substrates and products, as well as the thermodynamic constant, will vary variable depending on the antibiotic in question. Depending on the case they can vary between pH 4.5 and pH 8.5 and a temperature between −10° C. and 50° C.

We point out again that only with very stable and active penicillin G acylase derivatives will it be possible to prevent these factors from very drastically limiting these margins.

As an indication, but not a restriction of the invention the following examples are given hereinafter:

EXAMPLE 100 ml. of a solution 10 mM of 6 APA and 400 mM of phenylacetic acid in 50% dioxane/50 of acetate 50 mM, is prepared at a pH of 7. At the same time, a column therstatized to 37° C. with 10 ml. of *K. citrophila* derivative prepared according to patent . . . is prepared. 50 ml. are allowed to pass at a flow of 50 ml/h to balance the column and at that moment the reaction mixture is recirculated. The pH is maintained with the help of a buffer. The reaction is followed by HPLC, using a C-18 column and as a moveable phase 35% methanol/0.067M phosphate M 65% pH 4.7, measuring the absorbancy at 260 nm. It is left to recirculate until the balance is attained (we consider balance non-variation in the concentration of substrates or products for 1 hour.) In these conditions yields around 90% of conversion of 6-APA the penicillin G are obtained.

EXAMPLE 2

A solution of 15 mM of 7 ACA and 400 mM of thienylactic acid in 50% dioxane/50% acetate 50 mM is prepared at a ph 6. The column is thermostatized at 25° C., the flow and volume of the derivative are the same as in example 1. The moveable phase that we use for HPLC is 30% methanol/70% phosphate, 0.067M at a pH of 4.7, the rest of the conditions are maintained like those in example 1. After attaining the balance, the degree of conversion of 7-ACA into cephalothin is above 95%.

EXAMPLE 3

A solution of 10 mM of 6 APA and 120 mM of thienyl acetic acid in a mixture of 65% acetone /35% acetate 70 mM is prepared at a pH of 5.5. The column is thermostatized at 4° C. The other conditions are the same as those of the above examples. The conditions for HPLC are those of example 2. In these conditions, after reaching the balance, the conversion yields of 6 APA obtained are higher than 95%.

EXAMPLE 4

A solution of 40 mM of 6 APA and 200 mM of phenylacetic acid in 50% butanediol/50% acetate 50 mM is prepared at a pH of 6.5. The column is thermostatized at 4° C. The rest of the conditions are as in example 1. In these conditions, the degree of conversion of 6 APA to penicillin G is higher than 85%.

EXAMPLE 5

A solution of 4 mM of 7 ADCA and 80 mM of acetic acid in 70% ethanol/30% acetate 85 mM is prepared at a pH of 7.5. The reaction temperature is situated at 15° C. The rest of the conditions are as in example 4. In the balance, the degree of conversion of 7 ADCA is higher than 90%.

EXAMPLE 6

A solution of 110 mM of phenylacetic acid and 5.5 mM of 7 aminoacetoxycephalosporanic 2 (5-methyl-1,3,4 thiadiazol) (ADACAT) in 60% dimethylsulfoxide/40% acetate 65 mM is prepared at a pH of 7.5. The temperature at which the reaction is carried out is 20° C., the rest of the conditions are like in the other examples. In the balance the degree of conversion of 7 ADACAT was more than 95%.

EXAMPLE 7

A solution of 10 mM of 6 APA and 10 mM of phenylacetic acid in 50% dimethylformamide/50% acetate 50 mM is prepared at a pH of 5. The reaction temperature was 4° C. All the other conditions are like those in the above example. The degree of conversion of 6 APA obtained was higher than 55%.

EXAMPLE 8

A solution of 4.5 mM of 7 ACA and 200 mM of tienil acetic acid in 65% dioxane/35% acetate 70 mM is prepared at a pH of 8. The temperature at which the reaction is carried out is 10° C. The other conditions are those of example 2. The degree of conversion of the 7 ACA obtained exceeds 95%.

EXAMPLE 9

A solution of 10 mM of 6 APA and 10 mM of phenylacetylglycine in 50% dimethylformamide/50% acetate 50 mM is prepared at a pH of 5. The reaction temperature was 4° C. All the other conditions are like those of the above example. The degree of conversion of 6 APA obtained was higher than 55%.

We claim:

1. A method for the synthesis of a semi-synthetic antibiotic which can act as a substrate of penicillin G acylase or derivatives thereof where said semi-synthetic antibiotic is selected from the group consisting of hydroxypenicillins, cephmandol, penicillins, cephalosporins and semi-synthetic monobactamics, said method comprising direct condensation of the carboxyl group of the side chain of an acyl donor and the amino group of an antibiotic nucleus using penicillin G acylase, wherein said condensation occurs in a thermodynamically controlled system in an aqueous medium which comprises 30 to 90% of an organic cosolvent and an immobilized penicillin G acylase derivative, said immobilization achieved by multiple covalent union of the said derivative to free aldehyde groups of a support, wherein the reactants of said condensation comprise an antibiotic nucleus concentration between 0.5 and 875 mM, and an acyl donor concentration between 0.2 mM and 1M, said concentrations selected such that the antibiotic nucleus/acyl donor molar ratio is between $5 > 10^{-4}$ and 1.5, said condensation being carried out at a pH between 4.5 and 8.5, at a temperature between $-10°$ C. and $50°$ C., and with a buffer concentration between 0 and 1M; where said method results in at least about 85% recovery of said semi-synthetic antibiotic.

2. A method according to claim 1, wherein said penicillin G acylase is obtained from a microorganism selected from the group consisting of *Escherichia coli, Kluyvera citrophila, Bacillus magaterium* and *Proteus rettgeri*.

3. A method according to claim 2, wherein said support used for the immobilization of penicillin G acylase comprises a material selected from the group consisting of agar gels, agarose gels, cellulose, silica, porous glass, alumina, and synthetic acrylic resin particles, said material comprising free aldehyde groups formed by oxidation of the glycol groups with periodate.

4. A method according to claim 3, wherein said support material is agar or agarose and said support is prepared by etherification of agar or agarose gel with 2,3-epoxypropanol in strongly basic media and in the presence of an amount of boron hydride higher than 1 mg/ml.

5. A method according to claim 3, wherein the concentration of free aldehyde groups of the support used to immobilize penicillin G acylase is between 1 and 1000 μ equivalent per ml of support, and said concentration of free aldehyde groups corresponds to a surface density between 5 and 25 free aldehyde groups per 1000 $Å^2$ of support surface.

6. A method according to claim 4, wherein said immobilization of penicillin G acylase results in a surface density of free aldehyde groups between 10 and 25 aldehyde residues per 1000 $Å^2$ of support wherein said support is activated through reduction with boron hydride present at a concentration between 0.1 and 2 mg/ml, the reduction time is between 15 minutes and 2 hours, and the reduction temperature is between 4° and 30° C.; and the reaction between the resulting activated support and said penicillin G acylase occurs in a medium pH which is between 9 and 10, with a contact time between 30 minutes and 24 hours, at a reaction temperature between 4° and 300° C., and in the presence of penicillin G sulfoxide at a concentration between 0.5 and 10 mM.

7. A method according to claim 1, wherein said cosolvent is selected from the group consisting of dimethylformamide, acetone, isopropyl alcohol, dioxane, tetrahydrofuran and any apolar solvent that at concentrations of 50% in said medium cause an increase of more than one unit of pH in the pK of phenylacetic acid.

8. A method according to claim 1, wherein the antibiotic nucleus is a β-lactamic ring.

9. A method according to claim 8, wherein said β-lactamic ring is selected from the group consisting of 6-aminopenicillanic acid (6 APA), 7-aminocephalosporanic acid (7ACA), 7-amino-3-desacetoxycephalosporanic acid (7ADCA), 7-(2'-thienylacetamido)-3-desacetoxycephalosporanic acid (7ADACAT), and 7-phenylacetamido-3-desactoxycephalosporanic acid (7ADACAP).

10. A method according to claim 1, where the antibiotic nucleus is a monobactamic ring.

11. A method according to claim 10, wherein the monobactamic ring is 3AMB.

12. A method according to claim 1, wherein the acyl donor has the structure Ring—CHX—COOH, where X is selected from the group consisting of H, OH, $CH_3$, $NH_2$, and COOH.

13. A method according to claim 12, wherein Ring is selected from the group consisting of a simple aromatic nucleus and a hydrophobic ring.

14. A method according to claim 1, wherein the synthesized antibiotic is a semi-synthetic antibiotic having an unsubstituted methylene group in the ortho-position with respect to said side chain.

15. A method according to claim 1, wherein the synthesized antibiotic is cephalothin.

* * * * *

UNITED STATES PATENT AND TRADEMARK OFFICE
CERTIFICATE OF CORRECTION

PATENT NO. : 5,268,271
DATED : December 7, 1993
INVENTOR(S) : Jose M. Guisan Seijas, et. al.

It is certified that error appears in the above-indentified patent and that said Letters Patent is hereby corrected as shown below:

Title page, item [73], Assignee: change "Cosejo Superior De Invetigaciones Certificas" to --Consejo Superior de Investigaciones Cientificas--.

Title page, item [63], Application Data, change "Continuation of PCT/01/000, 146, Dec. 12, 1990". to --Continuation of PCT/ES90/00046, Dec. 12, 1989--.

Column 1, lines 9-10, change "This application is a continuation of PCT 01/000,046, filed Dec 12, 1990". to -- This application is a continuation of PCT/ES90/00046, filed Dec. 12, 1989--.

Signed and Sealed this

Twenty-sixth Day of April, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO.  : 5,268,271
DATED       : December 7, 1993
INVENTOR(S) : Jose M. Guisan Seijas, Robert Fernandez Lafuente, Gregorio Alvaro. Campos, Rosa M. Blanco Martin and Cristina Molina It is certified that error appears in the above-indentified patent and that said Letters Patent is hereby corrected as shown below:

On the title page, Item [73] should read :   Consejo Superior de Investigaciones Cientificas. --

On the title page, item [63], Related U.S. Application data, delete the current information and replace with -- Continuation of PCT/ES90/00046, December 12, 1990 --.

On the title page, add item [30], Foreign Application Priority Data, as follows

-- Dec. 12, 1989 [ES] Spain ........ P8904193 --

Column 1, lines 9-10, delete the current information and replace with

-- This application is a continuation of PCT/ES90/00046, filed Dec. 12, 1990. --

This certificate supersedes Certificate of Correction issued April 26, 1994.

Signed and Sealed this

Twenty-first Day of February, 1995

Attest:

BRUCE LEHMAN

*Attesting Officer*       *Commissioner of Patents and Trademarks*